(12) United States Patent
Boyadgis et al.

(10) Patent No.: US 12,016,421 B2
(45) Date of Patent: Jun. 25, 2024

(54) VISUAL COMMUNICATION SYSTEM FOR A HELMET

(71) Applicant: GoPro, Inc., San Mateo, CA (US)

(72) Inventors: Alfred Boyadgis, Haymarket (AU);
Julian Chow, Haymarket (AU);
Sebastian Adams, Annandale (AU);
Joseph Azar, Five Dock (AU);
Thomas Larcher, Mosman (AU)

(73) Assignee: GoPro, Inc., San Mateo, CA (US)

( * ) Notice: Subject to any disclaimer, the term of this patent is extended or adjusted under 35 U.S.C. 154(b) by 73 days.

(21) Appl. No.: 17/602,860

(22) PCT Filed: Apr. 20, 2020

(86) PCT No.: PCT/AU2020/050386
§ 371 (c)(1),
(2) Date: Oct. 11, 2021

(87) PCT Pub. No.: WO2020/210879
PCT Pub. Date: Oct. 22, 2020

(65) Prior Publication Data
US 2022/0031006 A1 Feb. 3, 2022

(30) Foreign Application Priority Data
Apr. 18, 2019 (AU) .............................. 2019901359

(51) Int. Cl.
*A42B 3/30* (2006.01)
*A61B 5/00* (2006.01)
(Continued)

(52) U.S. Cl.
CPC .............. *A42B 3/30* (2013.01); *A61B 5/6803* (2013.01); *G08B 5/36* (2013.01); *G08G 1/0104* (2013.01); *G08G 1/09* (2013.01)

(58) Field of Classification Search
CPC ....... A42B 3/30; A42B 3/0433; A61B 5/6803; G08B 5/36; G08G 1/0104; G08G 1/09
See application file for complete search history.

(56) References Cited

U.S. PATENT DOCUMENTS

| 7,168,095 B2 * | 1/2007 | Wright | ................... A41D 13/11 2/430 |
| 8,350,486 B2 * | 1/2013 | Bucalo | ................ B60Q 1/2676 362/249.05 |

(Continued)

FOREIGN PATENT DOCUMENTS

| EP | 1515295 A2 | 3/2005 |
| JP | 2000284214 | 10/2000 |

(Continued)

OTHER PUBLICATIONS

PCT International Search Report and Written Opinion, PCT Application No. PCT/AU2020/050386, Jul. 14, 2020, 12 pages.

*Primary Examiner* — John A Tweel, Jr.
(74) *Attorney, Agent, or Firm* — Young Basile Hanlon & MacFarlane, P.C.

(57) ABSTRACT

The present disclosure relates to a visual communication system for a helmet comprising: an array of light emitting devices arranged inside the helmet in a manner such that light emitted by the light emitting device is visible by a user of the helmet; a data communication interface arranged to receive situational related data from one or more sources; and a processing module arranged to process the situational related data and generate a light signal providing driving or riding guidance to the user of the helmet.

21 Claims, 6 Drawing Sheets

(51) Int. Cl.
  *G08B 5/36* (2006.01)
  *G08G 1/01* (2006.01)
  *G08G 1/09* (2006.01)

(56) References Cited

U.S. PATENT DOCUMENTS

| | | |
|---|---|---|
| 9,445,639 B1 | 9/2016 | Aloumanis et al. |
| 9,451,802 B2* | 9/2016 | Shearman ................. H04N 5/91 |
| 9,737,104 B1* | 8/2017 | Harris ................... G03B 17/561 |
| 9,749,515 B2* | 8/2017 | McCauley ............. G08C 17/02 |
| 10,368,602 B2* | 8/2019 | Dodson ................ A42B 3/0426 |
| 2013/0214998 A1* | 8/2013 | Andes ..................... G06F 3/044 |
| | | 345/8 |
| 2013/0257688 A1 | 10/2013 | Yamazaki et al. |
| 2017/0287441 A1 | 10/2017 | McKendrick |
| 2017/0329139 A1 | 11/2017 | Shearman et al. |
| 2021/0278666 A1* | 9/2021 | Foley ................... G09G 3/3426 |

FOREIGN PATENT DOCUMENTS

| | | |
|---|---|---|
| JP | 2002264874 | 9/2002 |
| JP | 2005067367 A | 3/2005 |
| JP | 2009042896 | 2/2009 |
| JP | 2015535972 | 12/2015 |
| WO | 2012040386 | 3/2012 |

\* cited by examiner

VISUAL COMMUNICATION SYSTEM FOR A HELMET

RELATED APPLICATION

This application claims priority to Australian provisional patent application No 2019901359 filed 18 Apr. 2019, which is herein incorporated by reference in its entirety.

TECHNICAL FIELD

The present technology relates to a visual communication system for use with a helmet.

BACKGROUND

Helmets are the most important item of protection for motorcycle riders, pilots and racing car drivers. Helmet users often don't have a direct access to navigational and traffic aids as regular car drivers may have through their infotainment systems.

Helmets that provide users with aids using audio messages through speakers embedded in the helmet shell do exist in the art. However, it would be recognised that audio aids are less immediate than visual signals and may not be suitable in situations where the user needs to make a quick decision.

To address this problem, military aircraft helmets employ a head mounted display (HMD) that projects information towards the eye of the pilot to provide full situation awareness and guidance. Military helmets, however, are very expensive and HMDs are not widely used in the motorcycle or car racing industry.

The technology relates to an improved helmet.

SUMMARY

In accordance with the first aspect, the present invention provides a visual communication system for a helmet comprising:
an array of light emitting devices arranged inside the helmet in a manner such that light emitted by the light emitting devices is visible to a user of the helmet;
a data communication interface arranged to receive situational related data—from one or more sources; and
a processing module arranged to process the situational related data and control the array of light emitting devices to generate a light signal providing riding or driving guidance to the user of the helmet.

In one embodiment, the array of light emitting devices is located outside of the user field of view and the generated light signal is directed towards a peripheral vision portion of the user. The array of light emitting devices comprises a plurality of light-emitting diodes (LED) devices.

In an embodiment, the LED devices are arranged to emit light with different colours with a colour being associated with one or more categories of riding/driving guidance.

In embodiments, the light emitting devices are configured to emit specific light patterns, each pattern being associated with a specific driving or riding aid.

In embodiments, the system comprises one or a combination of movement sensors, orientation sensors, positioning sensors or imaging devices. The movement sensors may comprise an accelerometer or a gyroscope; the orientation sensors may comprise an electronic compass; the positioning sensors may comprise a GPS receiver; and/or the imaging sensors may comprise one or more video-cameras. The one or more sensors may be arranged in the body of the helmet. One or more of the sensors may be external to the body of the helmet and communicate with the processing module via the data communication interface, using a wireless protocol. In some embodiments, the one or more sensors are arranged in the body of a vehicle being ridden/driven by the user.

In embodiments, the processing module is further arranged to analyse data received from the sensors in real time and provide riding/driving recommendations to the user.

In embodiments, the system comprises one or more speakers arranged to provide audio clues to the user, the audio clues being synchronised with the light signal.

In embodiments, the processing module is arranged to retrieve, via the data communication interface, traffic and/or weather-related data and process the retrieved traffic and/or weather-related data to provide improved driving or riding guidance to the user of the helmet.

In embodiments, the processing module is arranged to retrieve, via the data communication interface, rider/driver location related data and process the retrieved location related data to provide improved driving or riding guidance to the user.

In embodiments, the processing module switches between a track riding/driving mode, based on the retrieved location information, a city riding/driving mode and a mountain riding/driving mode.

In embodiments, the system further comprises a plurality of sensors located inside the helmet and arranged to measure one or more user health parameters. The one or more user health parameters may comprise one or a combination of: fatigue, focus, heart rate, pulse, eye movement, head movement.

In accordance with a second aspect, the present invention provides a helmet comprising:
an impact resistant shell;
a crash protection assembly including energy absorbing elements;
a visual communication system in accordance with the first aspect.

In an embodiment, the array of light emitting devices and the data communication interface are arranged inside a chin portion of the helmet. The chin portion hosting the light emitting devices and the data communication interface may be waterproofed.

In embodiments, the helmet comprises a camera arranged to film the environment in the field of view of the user. A replaceable transparent shield may be used to protect the camera.

In some embodiments, the helmet comprises a crash resistant battery.

In accordance with the third aspect, the present invention comprises, a method of providing riding or driving guidance to a rider or a driver wearing a helmet that comprises a visual communication system in accordance with the first aspect; the method comprising the steps of:
receiving situational related data form one or more sources via the data communication interface;
processing the situational related data via the processing module; and
controlling the array of light emitting devices to generate a light signal providing the rider or a driver.

In embodiments, the method further comprises the step of analysing, via the processor, data received from the sensors in real time and provide riding/driving recommendations to the user.

Advantageous embodiments of the present invention provide an in-helmet user guidance system that provides riding/driving cues to users without the need for a heads-up display or an eye mounted display.

The riding/driving cues are provided to the user through an integrated array of light emitting devices. The emitted light is directed in the user's peripheral field of view, so the user can see the riding/driving cues while focussing in the road ahead. This allows for a fast reaction to the everchanging riding/driving environment in all riding/driving circumstances.

The system provides access to an in-helmet advanced guiding platform technology to everyday motorbike riders and racing car drivers. The array of light emitting devices and control electronics are embedded in the chin-guard of the helmet and do not alter the normal external helmet profile/shape. Being almost invisible from the outside, the system does not cause safety issues or create aerodynamic inefficiencies for the helmet. The system leverages the processing power and data communication capabilities of the user mobile communication device to minimise the amount of hardware added to the helmet and the helmet battery life.

The majority of the electronics implementing the system is located in the chin portion of the helmet. The engineering of the electronics modules in the chin portion allows for an easier and less expensive safety certification process of the helmet, as the protection requirements for the chin portion are less stringent than the shell portion.

BRIEF DESCRIPTION OF THE DRAWINGS

Notwithstanding any other forms which may fall within the scope of the present invention, to make the technology more clearly understood, an embodiment of the technology will now be described, by way of example only, with reference to the accompanying drawings in which:

FIG. 4 (a) through 4(d) show illustrations of the in-helmet visual system in use.

DETAILED DESCRIPTION OF EMBODIMENTS

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

Figure 1A:
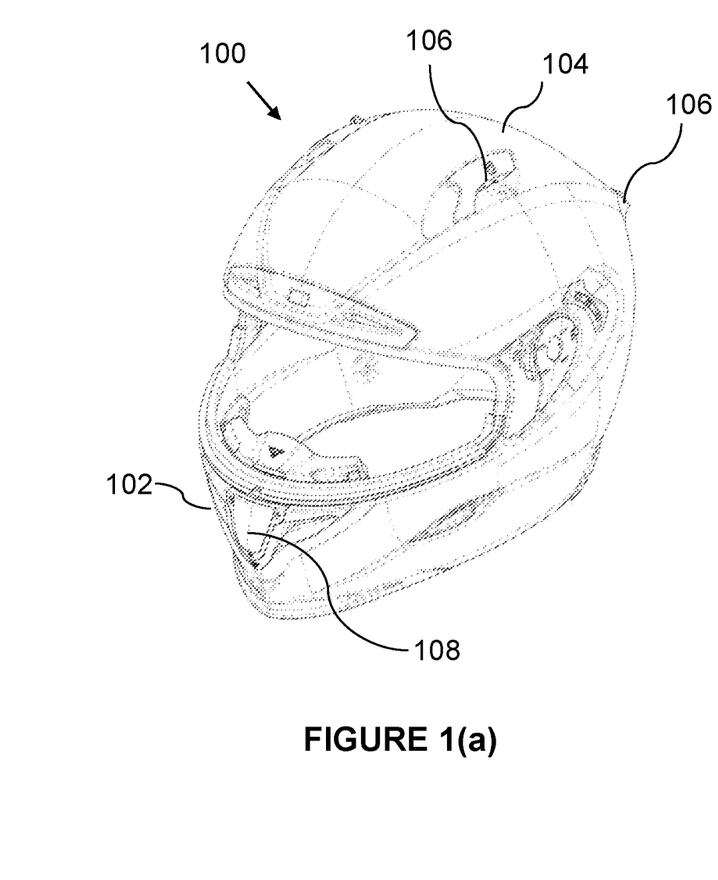
FIG. 1(a) and 1(b) shows schematic views of a motorcycle helmet embedding a system in accordance with embodiments.
Figure 1B:
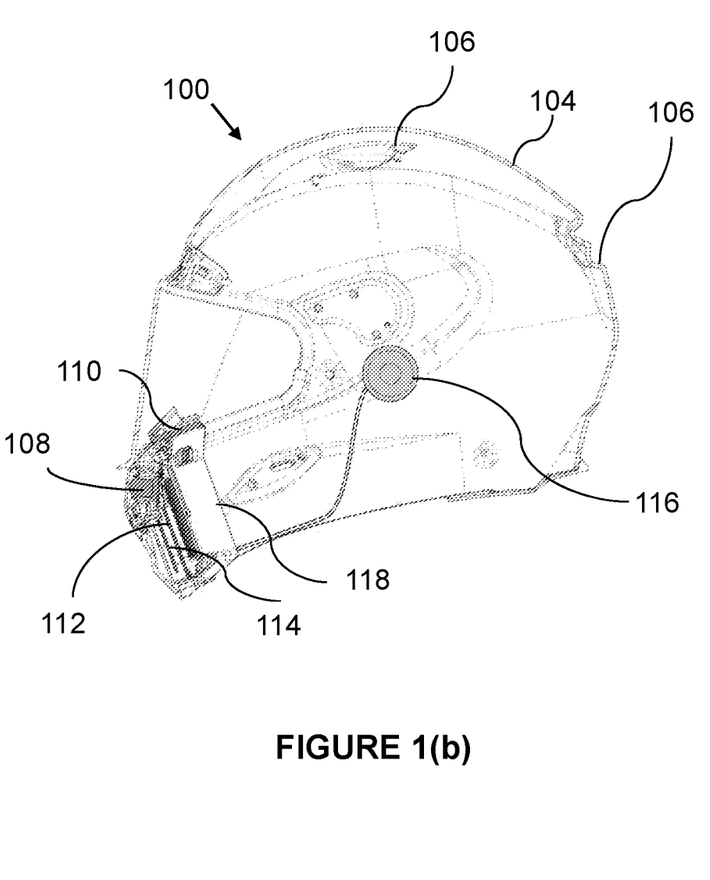

Referring now to FIG. 1 there are shown two side views of a motorcycle helmet 100 embedding a visual communication system embedded in the frontal portion of the helmet 102.

The helmet 100 has an impact absorbing shell 104, various air vents 106, and a forward mounted camera 108. The impact absorbing shell is preferably made of composite fiber. The air vents 106 allow drawing air flow into the helmet for cooling, as is especially experienced during high-speed downhill events. In embodiments, the air vents 106 may be selectively openable depending on the amount of ventilation required. The helmet 100 also comprises an internal lining for comfort purposes.

The visual communication system comprises an array of light emitting devices 110 that emit light in the visible spectrum which is visible to the helmet user. The system also comprises a camera control board 112 and a main electronic board that includes a data communication interface 114. The system is also connected to integrated speakers drivers 116 that can be used to provide audio aids to the helmet user.

The riding/driving cues are provided to the users in their peripheral field of view, so the user can see the riding/driving cues while focussing in the road ahead.

This allows for a fast reaction to the everchanging riding/driving environment in all riding/driving circumstances. The field of view is the outside world available to a user of a full-face helmet. If the user is directing eyes towards the road, the system is effective in their peripheral vision, therefore the users don't have to move their gaze to notice the light cues.

On full-face helmets, the viewing region is called the "eyeport". The light array is positioned so as not to obstruct the eyeport.

The data communication interface 114 includes a Bluetooth module arranged to be paired with a mobile communication device. In some embodiments a Wi-Fi module is also included in the communication interface 114. The data communication interface 114 is arranged to receive situational related data from one or more sources, including sensors external to the helmet 100. A processing module allows analysing the situational related data and generating light signals providing driving or riding guidance to the user of the helmet and a memory arranged to store riding/driving and/or navigational data.

Situational data are related to the vehicle, the rider and the surrounding environment. For example, situational related data could be speed of the vehicle, lean angle, weather data, GPS data or information incoming from a network, such as the internet.

The helmet also comprises a USB-C connector that can be used to charge the system battery, located in the helmet shell, or download data from the on-board memory.

Figure 2:
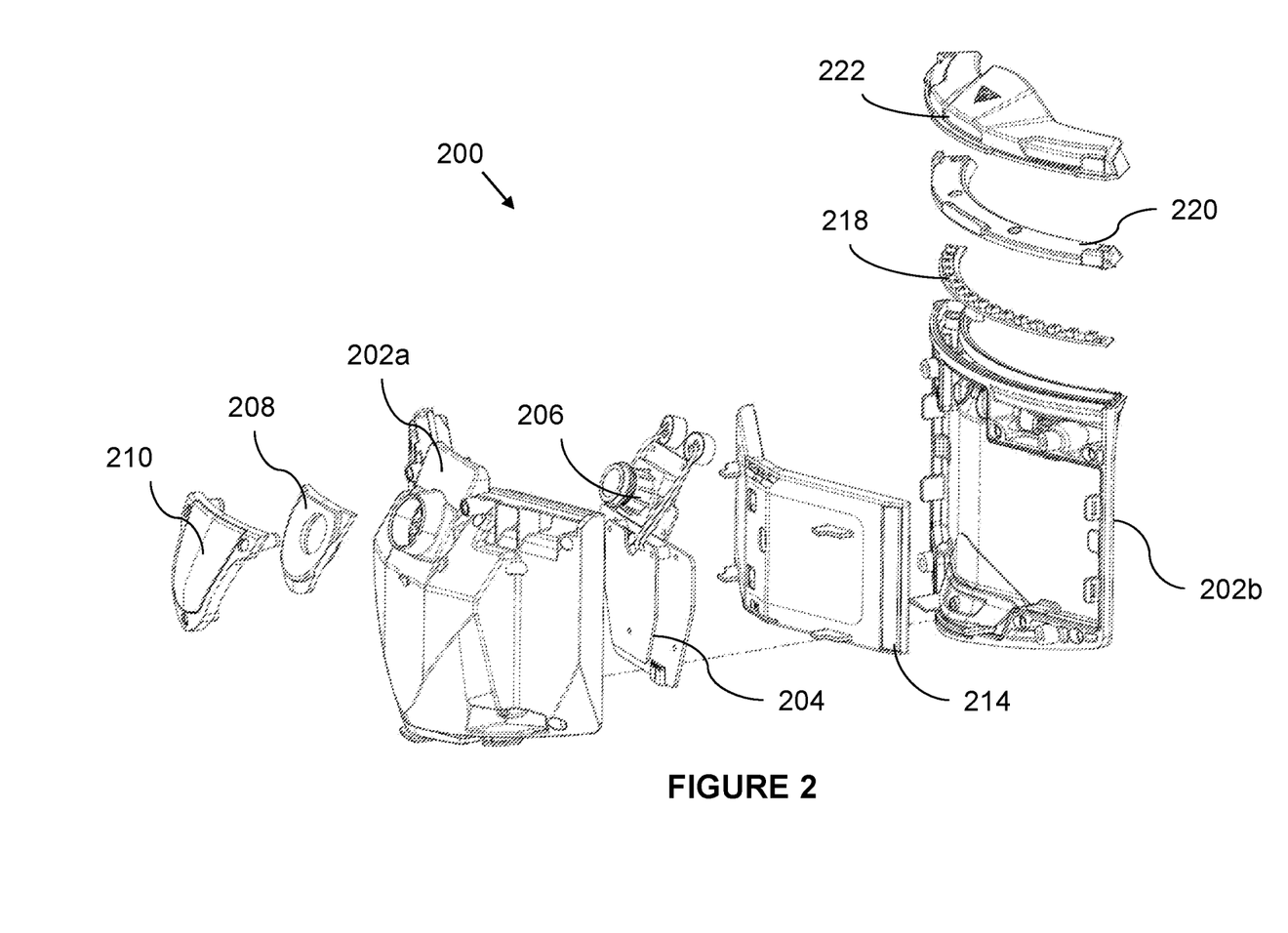
FIG. 2 shows an exploded view of a portion of the system in accordance with embodiments.

Referring now to FIG. 2, there is shown an exploded view of a visual communication module 200 in accordance with embodiments. The module 200 comprises a housing that houses the main electronic boards 204 and the camera module 206. The housing is made of a front panel 202a and a rear panel 202b that can be releasably fastened together. A gasket 208 mounted to the front of the housing prevents water from entering in the system. The camera supports a lens protector 210 that completes the camera 206 optical path.

The Module 200 also comprises a battery located in the battery housing 214 and an integrated battery control system. An array of light emitting devices, in this case a multi-colour LED array 218 lines the inner-upper edge of the helmet chin-bar, delivering informational alerts via the projection of light to the rider. The array supports a full spectrum of colour and is paired with a waveguide 220 inside the helmet and a waveguide cover 222 in a manner such that light emitted by the light emitting device is visible to the user.

The data communication interface is arranged on the main electronic board 204 which also comprises the processing unit and the memory, the Wi-Fi unit, the Bluetooth module, the LED array control unit and a Gyroscopic Unit.

Figure 3:
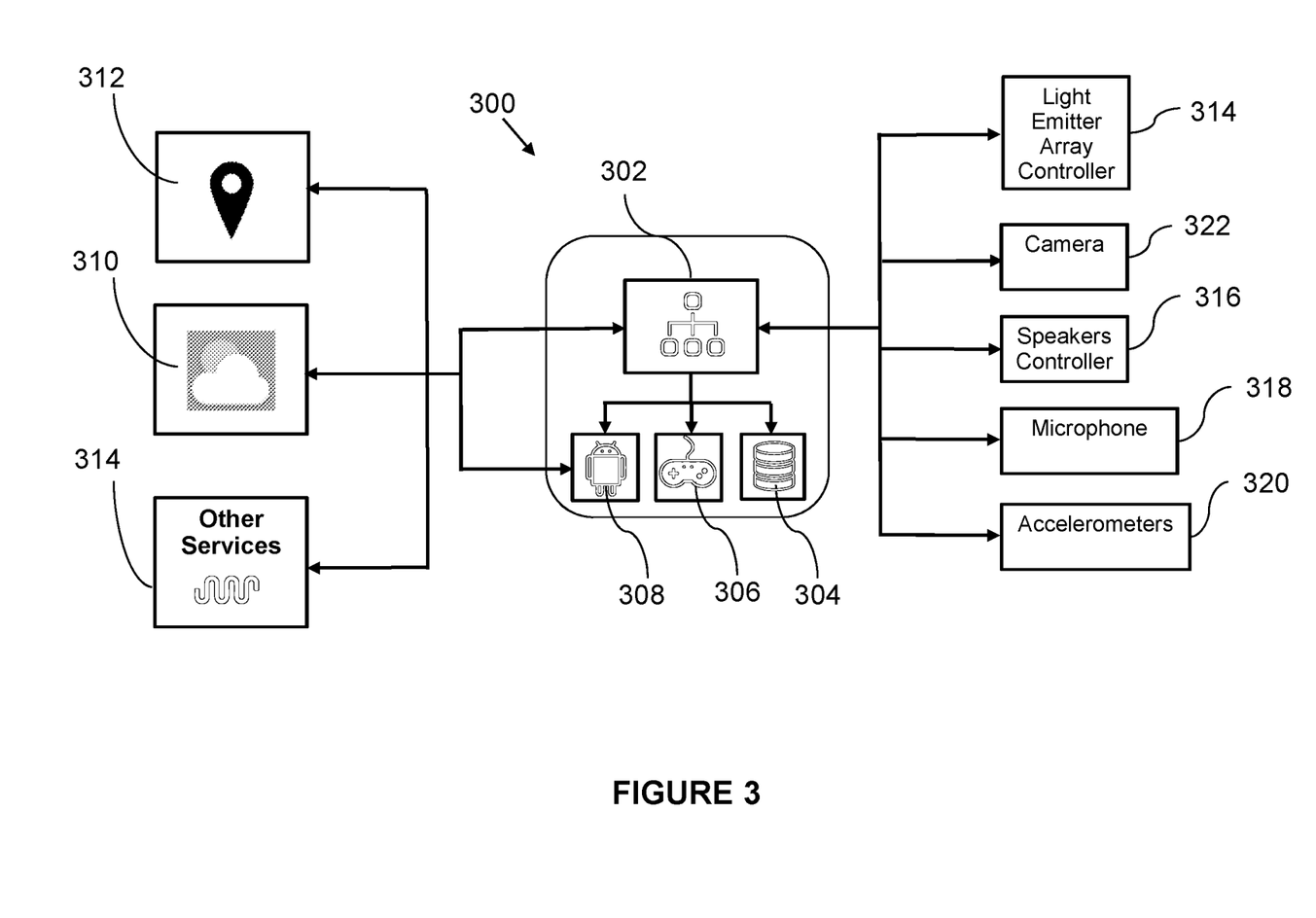
FIG. 3 shows a simplified block diagram of the visual communication system.

FIG. 3 shows a simplified block diagram 300 of the visual communication system in accordance with embodiments. The system command 302 processes information gathered via sensors and external data streams, coordinates data analysis and information sent to the helmet user via the LED array and, in some instances, the helmet speakers.

The system command 302 can be hosted entirely on a remote web server and communicate with the helmet via a mobile application 308 running on the user's mobile communication device. The system command 302 works in synergy and constant communication with a database 304, an optional controller 306 that can be located on-board the vehicle (for example handlebar of a motorbike) and the mobile application 308.

The database 304 houses all data utilised by the mobile application 308 and provides a storage location for all relevant user-generated data.

The mobile application 308 can be the single point of contact where the helmet can interact with the rich content services provided by the system command 302. The mobile application 308 is responsible for interfacing with the helmet and providing a control point for the peripherals. The mobile application 308 connects directly to the controller located on-board the vehicle 306.

The system command 302, can retrieve relevant data from a plurality of external data sources, such as weather data 310, navigational and/or traffic data 312 and/or additional data 314, such as local information and alerts. Data streams are sent to the mobile application 308 via the internet connection of the user's mobile communication device. The system command 302 is responsible for the aggregation of third-party data sources, database interaction, and computationally heavy procedures, whilst interacting directly with the mobile application 308.

Local weather forecasting data sources 310 are aggregated by the platform for the purpose of delivering location-specific weather information to the user.

Traffic and alerts data sources 312 are aggregated by the platform for the purpose of delivering location-specific traffic, hazard, and convenience information to the user.

Additional services/data sources 314 are aggregated by the platform for the purpose of delivering pertinent information to the user, relating to areas other than weather and/or traffic and alerts information.

The main electronic board connects to the LED array controller 314, the helmet speaker's controller 316, the microphone 318, and one or more accelerometers 320. The helmet connects directly to the mobile application 308, and is worn by the user, enabling them to leverage the on-board peripherals in conjunction with pertinent information delivered via the mobile application.

Motorbike riders have the option of controlling the peripherals and the helmet using a handlebar controller 306. The handlebar controller 306 can interface with the helmet via mobile application 308 or directly via the helmet Bluetooth module. The handlebar controller 306 provides a selection of control functions that are central to the operation of the helmet.

The outward-facing camera 322 allows for recording and playback directly within the mobile application 308 connected to the helmet.

The LED array is controlled, through controller 314 that is operated by the system command 302 through the user's mobile communication device and the software application 308. Riding/driving guidance is provided to the helmet user, through the LED array and it's based on all the information gathered via the data sources (weather, traffic and others), the on-board system sensors (camera, accelerometers, gyroscope, etc.) and vehicle on-board sensors (6 axes inertial system, braking force, G-force, velocity sensors, engine temperature, oil level, gas level, brake health, suspension setting).

Figure 4:
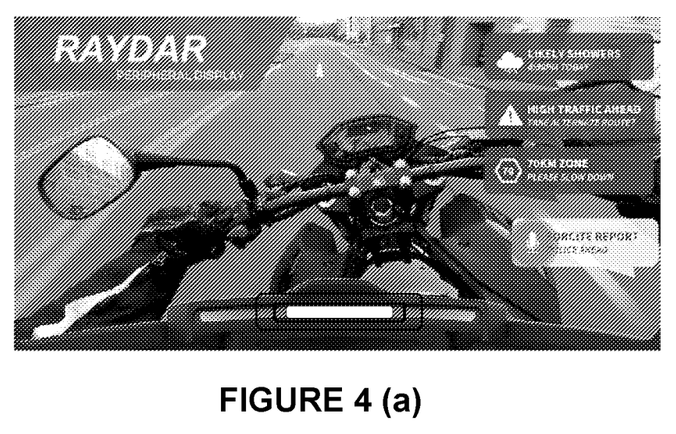

FIG. 4 shows the visual communication system of FIGS. 1 and 2 in operation. Using artificial intelligence, the system identifies the situations where it is warranted to provide riding/driving aids to the user.

Lighting patterns separate each alert type, providing easily discernible meanings for each cue. The on-board speakers can also enable the mobile application to present audio cues to the rider. The audio cues are synchronised with the light patterns.

The table below outlines the type of riding/driving cue provided by the helmet to the user in a number of situations.
  High-importance alert: blinking red light (FIG. 4 (a));
  Medium importance alert blinking yellow light;
  Navigation—turn: orange linking (right or left side of the array (FIG. 4(b));
  Police ahead: alternate blue and red (FIG. 4(c));
  Weather alert: blue (FIG. 4(d)).

|  | Colour | Pattern |
|---|---|---|
| Command/Audio | | |
| Helmet On | Green | Pulse once |
| Helmet Off | Red | Pulse twice |
| Battery Low | Red | Single flash |
| Helmet on charge/charging | Green | Pulse twice once connected to power |
| Pairing mode (BT seeking) | Blue | Constant flash until paired |
| WI_FI seeking | Purple | Constant flash until paired |
| Handle bar controller connected | Blue | Blue pulse |
| Navigation | | |
| Keep left | Green | Pulse twice left side |
| Keep right | Green | Pulse twice left side |
| Turn left | Green | Transition to right 3 times |
| Turn right | Green | Transition to right 3 times |
| Exit left | Green | Pulse once left side |
| Exit right | Green | Pulse once left side |
| Continue straight | Green | Transition from outside to center twice |
| Make a U-turn | Green | From right to left twice |
| Take the 1st Exit | Green | Pulse once |
| Take the 2nd Exit | Green | Pulse twice |
| Take the 3rd Exit | Green | Pulse thrice |
| Take the 4th Exit | Green | Pulse 4 times |
| Take the 5th exit | Green | Pulse 5 times |
| Merge Left | Green | Slow Transition to the Left |
| Merge Right | Green | Slow Transition to the right |
| Alerts | | |
| Weather alert (wind, storm, flooding) | Blue | Side to side |
| Traffic ahead | Yellow | Pulse twice |
| Heavy traffic ahead | Orange | Pulse twice |
| Hazard reported on road | Red | Pulse twice |
| Speed camera reported | Purple/white | Flash twice |
| Police reported in the | Blue and Red | Pulse from red to blue |

-continued

|  | Colour | Pattern |
| --- | --- | --- |
| vicinity | | |
| Sharp turns ahead proceed with caution | Orange and Yellow | Pulse from orange to yellow |
| Long straight ahead | Green | Pulse |
| Helmet | | |
| Video recording | Red | Pulse |
| Scanning area | White | Side to side |
| Mode change | | |
| Scenic mode | White | Pulse |
| Highway mode | White | Pulse |
| Street mode | White | Pulse |
| Low-light mode active | White | Pulse |
| Race mode active | Green | Pulse three times |
| Memory dump | Red | Pulse twice |

The system command stores structured information about helmet users, vehicle type, driver/rider ability and tracks user locations. Machine learning algorithms are used by the system command to provide tailored riding/guiding aids to the user through the helmet.

Different navigation type cues can be provided for different motorbike types. For example, timing of the riding aids would be different for superbike riders to delivery riders.

Sensor data collected by the helmet will determine: how frequently the user rides/drives the vehicle, braking patterns, center of balance, average speed, behaviour patterns. Through machine learning, the system may learn riding/driving habits and adjust guidance accordingly. For example, for fast riders, the system may automatically turn on speed camera alerts. Storing location data allows the system to provide tailored riding/driving aids to the user by anticipating which routes the user will take and calculating travelling times.

Figure 5A:
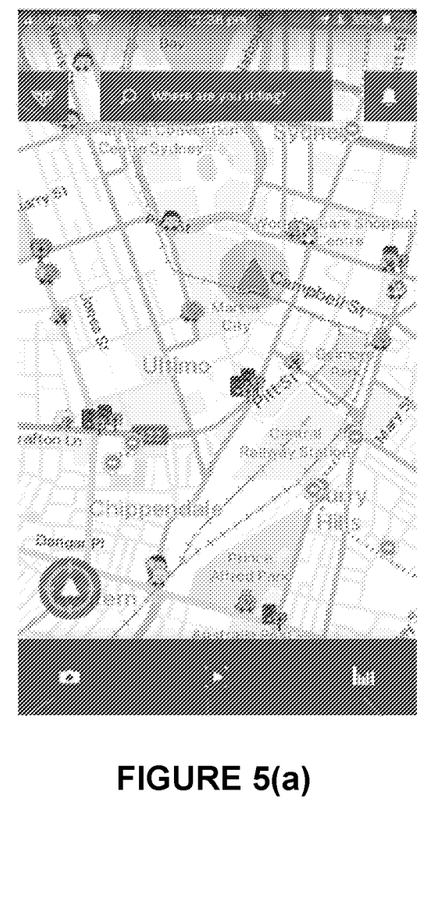
FIGS. 5(a) through 5(c), 6(a) and 6(b) show a number of views of the user interface provided by the software application linked to the visual communication system.
Figure 5B:
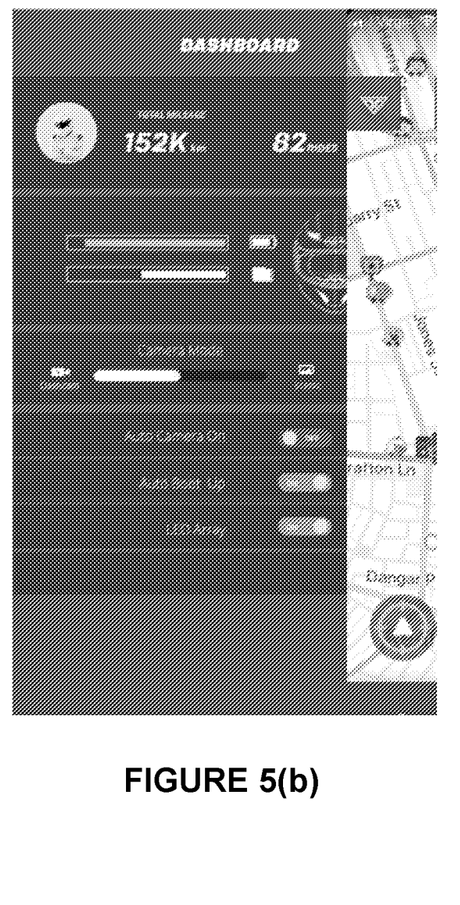
Figure 5C:
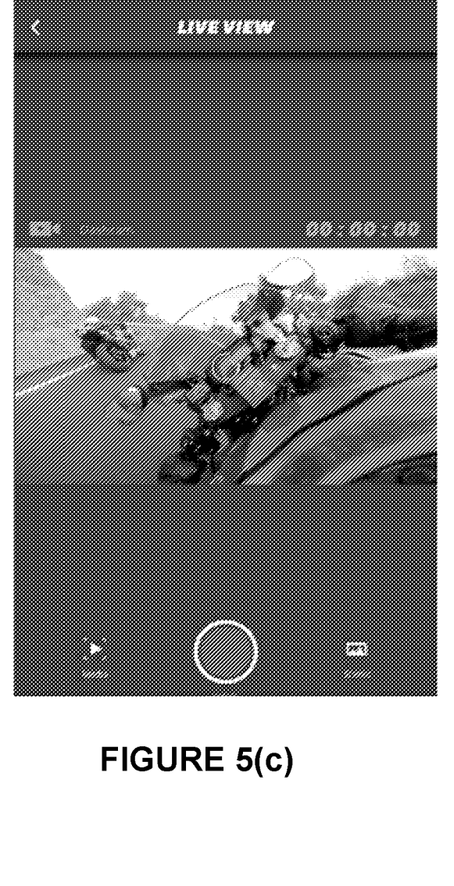

FIG. 5 shows a number of views of the user interface provided by a software application linked to the visual communication system. The application acts as an external control system to the helmet to access complex functions and settings. Connecting the helmet to the user personal phone also allows for quick sharing to social media and also audio streaming and navigation.

The navigation interface in FIG. 5(a) provides the rider/driver with the maps showing their current location, an address input for their destination and a shortcut to a list favourite locations. The rider can add new locations to their location list via text input. Maps can be generated by external online and offline sources to generate map coordinates and traffic alerts, such as Mapbox, Waze or Google.

FIG. 5(b) shows a dashboard interface that provides quick access to crucial controls and information such as helmet battery life, shortcuts to control core functions such as: camera mode, mileage counter and riding activity log that can be linked to social media profile.

FIG. 5(c) shows the live view interface or camera control page allows the user to see preview footage from their helmet camera. The live view interface can control the status of the camera, displays camera mode and time counter, allow access to helmet media and switching between scenic mode and dashcam mode. The camera function can also activate the GPS tracking at the same time storing location data and activity data such as speed and telemetry.

Figure 6A:
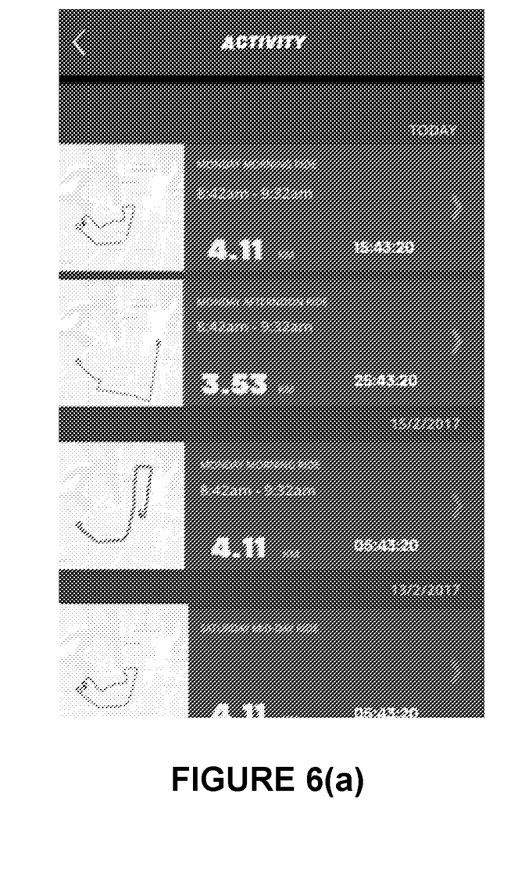

FIG. 6(a) shows the software application activity data interface. This interface shows a log of activities and routes taken while camera has been recording from start to finish (one ride). The latest ride is displayed on the top and the user can scroll down for older rides. As each Ride is correlated to a video file, the ride can be deleted by deleting the correlated video file.

Figure 6B:
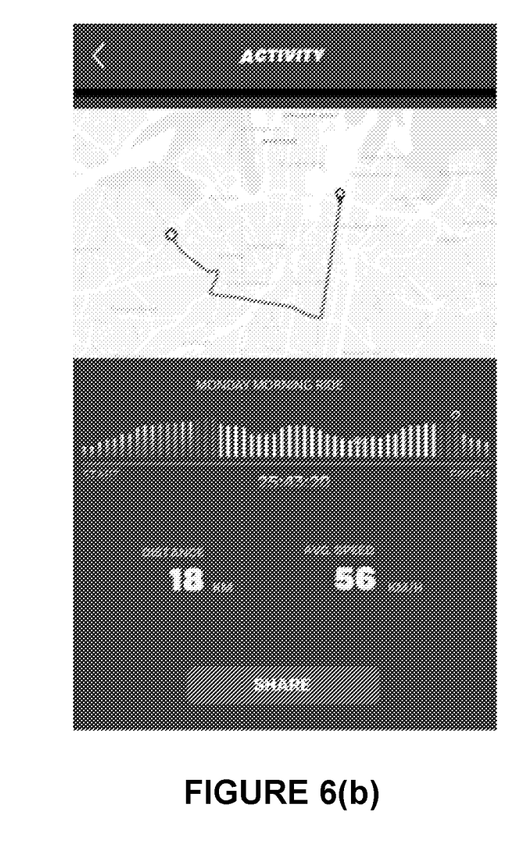

FIG. 6(b) shows the software application analytics interface. By selecting one of the "rides", this interface provides a breakdown of route taken, approximate distance travelled and a timeline of activity. A third party enabled map can zoom in and out for detailed review, timeline infographic shows where there is high level of telemetry movement. For example, if high amount of lean or sudden braking is detected, it will be logged and highlighted on the timeline. Ride information can also be shared to social media.

Throughout this specification the term "comprise", or variations such as "comprises" or "comprising", will be understood to imply the inclusion of a stated element, integer or step, or group of elements, integers or steps, but not the exclusion of any other element, integer or step, or group of elements, integers or steps. The term 'consisting of' means consisting only of.

Any discussion of documents, acts, materials, devices, articles or the like which has been included in the present specification is solely for the purpose of providing a context for the present technology. It is not to be taken as an admission that any or all of these matters form part of the prior art base or were common general knowledge in the field relevant to the present technology as it existed before the priority date of each claim of this specification.

Unless the context requires otherwise or specifically stated to the contrary, integers, steps, or elements of the technology recited herein as singular integers, steps or elements clearly encompass both singular and plural forms of the recited integers, steps or elements.

In the context of the present specification the terms 'a' and 'an' are used to refer to one or more than one (i.e., at least one) of the grammatical object of the article. By way of example, reference to 'an element' means one element, or more than one element.

Those skilled in the art will appreciate that the technology described herein is susceptible to variations and modifications other than those specifically described. It is to be understood that the technology includes all such variations and modifications. For the avoidance of doubt, the technology also includes all of the steps, features, and compounds referred to or indicated in this specification, individually or collectively, and any and all combinations of any two or more of said steps, features and compounds.

It will be appreciated by persons skilled in the art that numerous variations and/or modifications may be made to the technology as shown in the specific embodiments without departing from the spirit or scope of technology as broadly described. The present embodiments are, therefore, to be considered in all respects as illustrative and not restrictive.

The invention claimed is:

1. A visual communication system for a helmet comprising:
   a visual communication module configured to be embedded within a housing disposed in a chin portion of the helmet, wherein the visual communication module comprises:
      an array of light emitting devices disposed in the housing such that light emitted by the light emitting devices is visible to a user of the helmet, the array of light emitting devices being positioned so as not to obstruct an eyeport of the helmet;

a data communication interface arranged to receive situational related data from one or more sources;

a processing module arranged to process the situational related data and control the array of light emitting devices to generate a light signal providing riding or driving guidance to the user of the helmet; and a camera arranged to film the environment in a field of view of the user, wherein the housing comprises a front panel and a rear panel that are releasably fastenable to one another, wherein the light emitting devices are configured to emit light patterns, at least one of the light patterns being associated with a driving or riding aid, and wherein the generated light signal is directed towards a peripheral vision portion of the user.

2. The system of claim 1, wherein the array of light emitting devices comprises a plurality of light-emitting diodes (LED) devices.

3. The system of claim 2, wherein the LED devices are arranged to emit light with different colors with a color of the colors being associated with one or more categories of riding/driving guidance.

4. The system of claim 1, wherein the system comprises one or a combination of movement sensors, orientation sensors, positioning sensors or imaging devices.

5. The system of claim 4, wherein:
the movement sensors comprise an accelerometer or a gyroscope; the orientation sensors comprise an electronic compass;
the positioning sensors comprise a GPS receiver; or
the imaging devices comprise one or more video-cameras.

6. The system of claim 4, wherein one or more sensors are arranged in the body of the helmet.

7. The system of claim 4, wherein one or more of the sensors are external to the body of the helmet and communicate with the processing module via the data communication interface, using a wireless protocol.

8. The system of claim 7, wherein the one or more sensors are arranged in the body of a vehicle being ridden/driven by the user.

9. The system of claim 4, wherein the processing module is further arranged to analyze data received from the sensors in real time and provide riding/driving recommendations to the user.

10. The system of claim 4, further comprising one or more speakers arranged to provide audio clues to the user, the audio clues being synchronized with the light signal.

11. The system of claim 4, wherein the processing module is arranged to retrieve, via the data communication interface, traffic and/or weather-related data and process the retrieved traffic and/or weather-related data to provide improved driving or riding guidance to the user of the helmet.

12. The system of claim 4, wherein the processing module is arranged to retrieve, via the data communication interface, rider/driver location related data and process the retrieved location related data to provide improved driving or riding guidance to the user.

13. The system of claim 12, wherein, based on the retrieved location information, the processing module switches between a track riding/driving mode, a city riding/driving mode and a mountain riding/driving mode.

14. The system of claim 4, wherein the system further comprises a plurality of sensors located inside the helmet and arranged to measure one or more user health parameters.

15. The system of claim 14, wherein the one or more user health parameters comprise one or a combination of: fatigue, focus, heart rate, pulse, eye movement, head movement.

16. A helmet comprising:
an impact resistant shell;
a crash protection assembly including energy absorbing elements; and
a visual communication system, wherein the visual communication system is embedded within a chin portion of the helmet and comprises:
a data communication interface arranged to receive situational related data from one or more sources;
a processing module arranged to process the situational related data and control an array of light emitting devices to generate a light signal providing riding or driving guidance to the user of the helmet; and
a camera arranged to film the environment in a field of view of the user,
wherein the housing comprises a front panel and a rear panel that are releasably fastenable to one another to enclose the data communication interface, the processing module, and the camera such that the visual communication system does not alter an external profile shape of the helmet.

17. The helmet of claim 16, wherein the array of light emitting devices is arranged inside the chin portion of the helmet.

18. The helmet of claim 17, wherein the chin portion hosting the light emitting devices, the processing module, the camera, and the data communication interface is waterproofed.

19. The helmet of claim 16, further comprising a lens protector that protects the camera.

20. The system of claim 1, wherein the housing houses at least one main electronic board which comprises the data communication interface and the processing module.

21. The system of claim 20, wherein the at least one main electronic board and a camera module comprising the camera are housed between the front panel and the rear panel.

* * * * *